United States Patent [19]

Kuckertz et al.

[11] Patent Number: 4,564,712
[45] Date of Patent: Jan. 14, 1986

[54] PROCESS FOR THE PREPARATION OF DIPHENYL ETHERS

[75] Inventors: Herbert Kuckertz, Kelkheim; Georg Schaeffer, Hofheim am Taunus, both of Fed. Rep. of Germany

[73] Assignee: Hoechst Aktiengesellschaft, Frankfurt, Fed. Rep. of Germany

[21] Appl. No.: 554,378

[22] Filed: Nov. 23, 1983

Related U.S. Application Data

[63] Continuation of Ser. No. 315,933, Oct. 28, 1981, abandoned.

[30] Foreign Application Priority Data

Oct. 30, 1980 [DE] Fed. Rep. of Germany ....... 3040849

[51] Int. Cl.⁴ .............................................. C07C 41/16
[52] U.S. Cl. .................................... 568/635; 568/639; 568/433; 568/592; 260/465 F; 560/61
[58] Field of Search ............... 568/635, 639, 433, 592; 260/465 F; 560/61

[56] References Cited

U.S. PATENT DOCUMENTS 3,083,234  3/1963  Sax ..................................... 568/636

OTHER PUBLICATIONS

The Condensed Chemical Dictionary 8th Ed. (1971) 234.
Elenevskii et al., Chem. Abs. vol. 32 (1938) 7904.
M. A. Elenevskii et al., Zh. Obsc. Chim., vol. VIII, No. 6, pp. 507–509 (1938).
Gmelins Handbuch der Anorganischen Chemie—Kupfer-Teil B–Lieferung 2 (1961), Cover page and p. 663.

Primary Examiner—Bernard Helfin
Attorney, Agent, or Firm—Curtis, Morris & Safford

[57] ABSTRACT

Diphenyl ethers are prepared by Ullmann reaction of alkali metal phenolates with halobenzenes in the presence of basic copper carbonate and/or copper salts of lower aliphatic carboxylic acids as catalysts. These special catalysts have a better catalytic activity than other copper catalysts known for the Ullmann reaction.

The diphenyl ethers prepared or obtainable according to the invention are mainly intermediates in diverse fields such as pharmaceuticals or plant protecting agents.

10 Claims, No Drawings

PROCESS FOR THE PREPARATION OF DIPHENYL ETHERS

This application is a continuation of application Ser. No. 315,933 filed Oct. 28, 1981 and now abandoned.

Diaryl ethers, among them mainly the diphenyl ethers, are especially intermediates in diverse fields, such as those of pharmaceuticals and plant protecting agents. The m-phenoxytoluene diphenyl ether, for example, is the intermediate for the manufacture of insecticides of the pyrethroid type, which are distinguished by high insecticidal activity at low toxicity in warm-blooded animals.

A number of diverse methods is known for the preparation of diaryl ethers. An advantageous method usually applied is the so-called Ullmann reaction which consists in reacting alkali metal phenolates with aryl halides at elevated temperature in the presence of copper or copper compounds as catalysts (see Krauch-Kunz, Reaktionen der organischen Chemie, ed. D. Hüthig, Heidelberg, 1976, p. 320).

The Ullmann reaction in turn is known for having different embodiments (variation of starting materials, of the copper catalysts, of the reaction temperature, the solvents etc.). According to Houben-Weyl, Methoden der organischen Chemie, ed. G. Thieme, Stuttgart, 1965, vol. VI/3, page 86, the bromine compounds (aryl bromides) react more readily than the chlorine compounds. Only in the case where the aryl nucleus contains further determined activating groups the aryl chlorides are said to be sufficiently reactive. According to the prescriptions of this reference, Cu-powder is used as catalyst in the Ullmann reaction. The reaction temperature is indicated as being in the range of from 150° to 230° C. For some cases, excess phenol or dimethyl formamide is recommended as solvent or diluent. For example, bis-(4-methylphenyl)ether is said to be obtained with a yield of 87% of theory within about 2 hours from K-p-cresolate and 4-Br-toluene at 200° to 240° C. in the presence of Cu bronze as catalyst, or also from free p-cresol.

In Example 1 of German Offenlegungsschrift No. 2,228,609, a catalyst mixture of CuCl, $CuCl_2$, $CuCO_3.Cu(OH)_2.H_2O$, Cu-powder and activated $Al_2O_3$ is used for the Ullmann reaction of the potassium salt of bisphenyl-4-ol with p-chlorotoluene. At temperatures of up to 230° C., 76% of theory of p-bisphenyloxytoluene are thus obtained in a reaction time of 30 hours.

In German Offenlegungsschrift No. 2,242,519, several copper compounds (CuO, $Cu_2O$, $CuCO_3$, CuCl, $CuCl_2$, CuBr etc.), among them also basic copper carbonate, are indicated as catalyst for the operation mode described there, although in all examples CuO only was used as catalyst. At reaction temperatures of from 120° to 200° C. and in the presence of up to 50 Mol-% of the corresponding free phenol (on which the alkali metal phenolate used is based), yields of about 60 to 75% of theory of the specific diphenyl ethers are said to be obtained according to the examples within several hours of reaction time. Preferably copper powder, but also oxides, carbonates, chlorides, bromides or sulfates of copper are furthermore cited in Published French Application No. 7,816,746 (No. of publication 2,392,950) as catalysts for the Ullmann reaction. According to the reaction variant described there, large excesses of free phenol (on which the corresponding alkali metal phenolate is based) are said to be used above all.

In a similar manner proceeds the process of Belgian Pat. No. 874,981 for preparing m-phenoxytoluene by Ullmann reaction of alkali metal m-cresolate with chlorobenzene in the presence of CuCl as catalyst (at 150°–170° C.) and excess m-cresol.

Although the known operation modes of the Ullmann reaction for the preparation of diaryl ethers in general proceed rather satisfactorily, in view of the general efforts for process optimization it was nevertheless the object of the invention to improve the processes further and to make them still more economic. This object was achieved by selection of quite special copper catalysts, that is, basic copper carbonate and/or copper salts of lower aliphatic carboxylic acids.

Subject of the invention is therefore a process for the preparation of diphenyl ethers by reaction of alkali metal phenolates with halobenzenes at elevated temperature and in the presence of copper compounds as catalysts, which comprises using basic copper carbonate and/or copper salts of lower aliphatic carboxylic acids as copper compounds.

Suitable basic copper carbonates are in principle any basic copper carbonates of various compositions or varying water content. Examples of such basic copper carbonates are $2CuCO_3.Cu(OH)_2$, $CuCO_3.Cu(OH)_2.H_2O$ etc.; the basic copper carbonate having the following composition: $CuCO_3.Cu(OH)_2.\frac{1}{2}H_2O$ being a preferred compound.

As copper salts of lower carboxylic acids there are used above all the Cu II salts of aliphatic $C_1$–$C_3$ carboxylic acids (that is, of formic, acetic and propionic acid); the Cu II salt of $C_2$-carboxylic acid = copper acetate being preferred.

The copper catalyst can be employed per se or as mixtures with one another.

The preferred range of amounts is from about 0.0001 to 5, especially 0.001 to 0.1, mol-%, relative to the alkali metal phenolate.

The catalysts used in accordance with the invention in the Ullmann reaction have especially a considerably increased activity as compared to the other known copper catalysts, which at identical molar amounts results in a pronounced reduction of the reaction time, or, at identical amounts and reaction times, brings about increased conversion rates and yields.

It was extremely surprising to observe that the selection in accordance with the invention gives such an improved result, since according to the state of the art the occurrence of such considerable differences with respect to catalytic activity was not to be expected within the series of the known copper catalysts for the Ullmann reaction.

As starting alkali metal phenolates, any alkali metal phenolate may in principle be used for the process of the invention. Preferred are the sodium and potassium, especially the potassium, salts of unsubstituted phenol $C_6H_5OH$ as such, or phenol substituted one or several times, especially monosubstituted, in the nucleus. Suitable substituents are for example the following groups: lower alkyl ($C_1$–$C_4$-alkyl, preferably $CH_3$ or $C_2H_5$, especially $CH_3$), halogen (F, Cl, Br), CN, CHO, $CH(OR)_2$, COOR (R = lower alkyl).

Especially preferred alkali metal phenolates are the alkali metal salts of unsubstituted phenol and of phenol monosubstituted in o-, m- or p-position by lower alkyl or fluorine.

Suitable starting halobenzenes are either the monohalobenzene $C_6H_5Hal$ (Hal=Cl or Br, preferably Cl), or halobenzenes substituted in the nucleus; the substituents being identical to those cited for the alkali metal phenolates. In the case where the substituents are likewise halogen (F, Cl, Br), the starting halobenzenes of course are di- or polyhalobenzenes, not monohalobenzenes. In this case, it depends on the molar ratio of alkali metal phenolate to halobenzene whether one or more halogen substituents react with the alkali metal phenolate. However, fluorine substituents do not react in this reaction, or to an insignificant extent only. Preferred halobenzenes are mono- and dichlorobenzenes, mono- and dibromobenzenes, or monochloro- or monobromobenzenes substituted by one lower alkyl group; especially preferred are monochloro- or monobromobenzene unsubstituted or substituted by one lower alkyl group; the chlorine compounds being particularly preferred.

An especially preferred embodiment of the invention is the following: one of the reactants alkali metal phenolate and halobenzene is used in the form of a compound monosubstituted by lower alkyl, and the other as unsubstituted compound (that is, reaction of alkali metal cresolate with monochlorobenzene, or alkali metal phenolate with monochlorotoluene).

In all other respects, the process of the invention is carried out in the manner usual for the Ullmann reaction. According to an exemplified operation mode, the alkali metal phenolate is first prepared by mixing alkali metal hydroxide (NaOH and/or KOH, preferably KOH) in solid form or dissolved in water with the corresponding phenol and the halobenzene. Dehydration can be ensured by means of a water separator with reflux while using the halobenzene as entrainer. Advantageously, an excess of the corresponding phenol and halobenzene is used because this facilitates the dehydration as well as the later condensation reaction (faster and complete conversion of the alkali metal hydroxide, easier agitation and filtration of the reaction mixture containing the alkali metal halide, no precipitation of alkali metal phenolate etc.).

The molar ratio of alkali metal hydroxide to the corresponding phenol to halobenzene is advantageously in the range of from about 1:1:1 to 1:3:3. Dehydration is usually carried out under normal pressure. However, in the case of using high-boiling halobenzenes, the mixture is dehydrated either under reduced pressure or under normal pressure with addition of a second entrainer such as toluene or xylene.

The catalyst is normally added after dehydration, although it may be added also before.

After addition of the catalyst, for example, the reaction mixture is advantageously maintained for several hours (sometimes a few minutes only) with agitation at a temperature of from about 50° to 200° C., preferably about 100° to 200° C., and especially about 130° to 170° C., until stating complete conversion, for example by measuring the alkali content. Within this period of time, the initial solution is converted to a suspension by precipitation of alkali metal halide.

The reaction being complete, the reaction mixture is worked up according to diverse methods. The alkali metal halide and the copper catalyst can for example be separated by filtration, and the filtrate be worked up by fractional distillation. The mixture of corresponding phenol and halobenzene forming the first runnings can be reused for further batches without separation into the components.

Another work-up technique is the following: water or dilute aqueous acid is added to the reaction mixture, so that the alkali metal halide and the catalyst are dissolved in the precipitating aqueous phase, and can thus be eliminated. The organic phase can be further worked up by fractionation in the same manner as the above filtrate. The process can be carried out batchwise or continuously.

The variant according to the invention of the known Ullmann reaction supplies the corresponding (optionally substituted) diphenyl ethers with high yields and—at identical molar catalyst amounts as in the known operation modes—in a reduced reaction time. The invention represents therefore a considerable progress.

The following examples illustrate the invention.

Example 1 comprises some comparative tests with identical molar amounts (same Cu contents) of other copper catalysts than those used in accordance with the invention; this Example with the comparative tests demonstrates clearly the superior catalytic activity of the catalysts used according to the invention.

EXAMPLE 1 with comparative tests

In tests (a) through (i), there were introduced in each case into a 1 liter four-necked flask:

63.75 g of 88% solid KOH=1 mol.

Under an $N_2$ atmosphere and with agitation, there were added 324 g of m-cresol=3 mols and 338 g of chlorobenzene=3 mols.

The mixture was dehydrated by means of a water separator with reflux under normal pressure. In each case, about 26 g of aqueous phase separated. The dehydration being complete, the water separator was replaced by a reflux condenser, and the organic phase in the water separator was fed back to the reaction flask. 0.01 mol each of the copper salts listed in the following Table were then added to the dehydrated solution. The 0.01 molar copper salt amount is always relative to the copper content (identical copper content!).

After a 4 hours' reflux reaction under normal pressure, that is, at about 140° C., the content of 3-phenoxytoluene was determined by gas chromatography, and the conversion of K-m-cresolate was stated titrimetrically with the use of 0.1N hydrochloric acid.

The results were the conversion rates of K-m-cresolate to 3-phenoxytoluene listed in the Table with a selectivity of more than 98%. This proves that $Cu(CO_3)\cdot Cu(OH)_2\cdot 0.5H_2O$ and $Cu(OAc)_2\cdot H_2O$, after a reaction time of 4 hours, yield a 2.76 times higher conversion rate than the other copper catalysts.

TABLE

| Test | Catalyst | (g) | % conversion KOH |
|---|---|---|---|
| (a)* | $CuCO_3\cdot Cu(OH)_2\cdot 0.5H_2O$ | 1.1 | 69 |
| (b)* | $Cu(OAc)_2\cdot H_2O$ | 1.99 | 69 |
| (c)** | mixed catalyst of | 0.44 | |
| | CuCl | | |
| | $CuCl_2\cdot 2H_2O$ | 0.22 | |
| | $CuCO_3\cdot CU(OH)_2\cdot 0.5H_2O$ | 0.16 | 25 |
| | Cu-powder | 0.17 | |
| | $Al_2O_3$ (activated) | 1.05 | |
| (d)** | CuCl | 0.99 | 25 |
| (e)** | $CuCl_2\cdot 2H_2O$ | 1.7 | 23 |
| (f)** | CuO | 0.79 | 9 |
| (g)** | Cu-powder | 0.63 | 4 |

TABLE -continued

| Fract. | amount (g) | Temp. (°C.) sump | (°C.) head | pressure (mm Hg) | reflux | content in area % GC[1] ClBz[2] | m-cr.[3] | 3-PT[4] |
|---|---|---|---|---|---|---|---|---|
| 1 | 1363 org. +51 H$_2$O | 110–195 | 91–132 | 760 | 1:1 | 98.6 | 1.1 | — |
| 2 | 178 | 100–110 | 46–92 | 35–9 | 1:1 | 56.2 | 43 | 0.6 |
| 3 | 744 | 110–115 | 92–94 | 10 | 1:1 | | 98.2 | 1.8 |
| 4 | 66 | 132–138 | 95–96 | 9 | 2:1 | | 95.7 | 4.3 |
| 5 | 43 | 138–142 | 96–138 | 9 | 2:1 | | 63.9 | 36.1 |
| 6 | 567 | 146–185 | 130–185 | 8–5.5 | 2:1 | | | 99.3 |

29 residue
6 cooling trap
69 losses (column hold-up, samples etc.)

[1]length of column 2 m, column material SE30, programmed temperature 70–280° C.
[2]chlorobenzene
[3]m-cresol
[4]3-phenoxytoluene

| Test | Catalyst | (g) | % conversion KOH |
|---|---|---|---|
| (h)** | CuSO$_4$ | 1.59 | 2 |
| (i)** | without catalyst | 0 | 0 |

*according to invention
**comparison

The following Example 2 demonstrates that under similar reaction conditions and with prolongation of the reaction time to 6 hours, the catalyst in accordance with the invention gives a practically quantitative K-m-cresolate conversion at practically quantitative selectivity towards 3-phenoxytoluene.

EXAMPLE 2

3-Phenoxytoluene from K-m-cresolate and chlorobenzene

There were introduced into a 4 liter glass four-necked flask:
224.4 g of solid KOH, 88% strength=3.52 mols.
Under N$_2$ atmosphere and with agitation, there were added
1,298 g of m-cresol=12 mols and
1,351 g of chlorobenzene=12 mols.

During the addition, the temperature rose from about 20° C. to 50°–60° C.

The mixture was dehydrated within 1½ hours by means of a water separator (water being above), charged previously with 200 g of chlorobenzene, under reflux at a sump temperature of 120°–136° C.

4 g of pulverulent CuCo$_3$.Cu(OH)$_2$.½H$_2$O (=0.017 mol) were then added to the mixture cooled to 130° C. Subsequently, the mixture was refluxed for 6 hours at 137°–142° C. under N$_2$ and with agitation. Subsequently, the water separator including the 89 g of aqueous phase and 180 g of organic phase (chlorobenzene) contained therein was removed.

After cooling to 40° C., 1,000 ml of water were added to the mixture remaining in the reaction flask (2,815 g). A pH of 7 was adjusted first by means of hydrochloric acid (0.273 mol of HCl), and then a pH of 1 for better phase separation.

The aqueous phase was separated and, in order to ensure phase separation on extraction with chlorobenzene, diluted with 2 l of water. After dilution, the batch was extracted twice with 250 ml each=278 g of chlorobenzene (water above).

By fractionation of the united organic phases (3,116 g) via a silver-coated Vigreux column, separation height 120 cm, inner diameter 2.5 cm, there were obtained:

A calculation of yield which comprises only the pure m-phenoxytoluene obtained in fraction 6, that is, 567 g 0.993=563 g=3.06 mols, and where there is calculated on the basis of area %=weight %, gives the following isolated yields:
79.4%, relative to chlorobenzene
85.7%, relative to m-cresol
86.7%, relative to KOH used (a GC-analytic determination of the 3-phenoxytoluene product in the mixture being distilled resulted in a practically 100% yield).

EXAMPLE 3

3-Phenoxytoluene from K-phenolate and 3-chlorotoluene

In a N$_2$ atmosphere, there were introduced into the reactor:
63.75 g of 88% solid KOH=1 mol.
With agitation, a solution of
282.3 g=3 mols of phenol in
379.7 g=3 mols of 3-chlorotoluene was added. The temperature rose from about 20° C. to about 40° C. during this addition. Subsequently, the mixture was dehydrated within about 1 hour by means of a water separator to which 83 g of 3-chlorotoluene were charged (about 27 ml of aqueous phase). Temperature in the flask: 123°–162° C.

After cooling to about 160° C., 1 g of CuCO$_3$.Cu(OH)$_2$.½H$_2$O (=0.004 mol) was added to the clear solution. A black solution was thus formed.

Subsequently, the mixture was heated for a total of 4 hours at 168°–170° C. with slight reflux. First a greenish, then a red suspension was thus formed. At the end of this period of time, 64 g of liquid (78 area % of 3-chlorotoluene, 18 area % of phenol) were present in the water separator. The weight of the reaction mixture was 705 g. After washing with 55 g of 3-chlorotoluene, 94 g of solvent-moist=75.5 g of dry salt mixture were suction-filtered from the reaction mixture. The weight of the organic phase was 654 g (pH 6–7 after addition of water). According to gas chromatography analysis with dodecane as internal standard, the organic phase contained 28.5 weight % of 3-phenoxytoluene=186 g=1.01 mol; that is, the yield is practically 100% relative to KOH used.

| GC analysis during the reaction: | | | | | |
| --- | --- | --- | --- | --- | --- |
| hours reflux | 0 | 1 | 2 | 3 | 4 |
| area % 3-phenoxytoluene | 0 | 23.7 | 28.0 | 28.1 | 28.0 |

This means that the reaction is practically complete after 2 hours.

EXAMPLE 4

4-Phenoxytoluene from K-phenolate and 4-chlorotoluene

Operations were as in Example 3; only 3-chlorotoluene was replaced by 4-chlorotoluene.

The reaction was carried out at very slight reflux, because otherwise there was foaming (166°–167° C.) During the reaction, the mixture had first a black color, became then violet, and finally a red-brown suspension was formed (689 g)=648 g of filtrate. After washing with 55 g of p-chlorotoluene 84 g of filter cake remained in solvent-moist state=72 g dry (pH of the organic phase 7–8 after addition of water). According to GC analysis with dodecane as internal standard, the organic phase contained 28.1 weight % of 4-phenoxytoluene=182 g=0.99 mol, that is, the yield relative to KOH used is practically 100%.

| GC analysis during the reaction: | | | | | | | |
| --- | --- | --- | --- | --- | --- | --- | --- |
| hours of reflux | 0 | 1 | 2 | 3 | 4 | 5 | 6 |
| area % 4-phenoxytoluene | — | 21.9 | 26.5 | 27.1 | 27.4 | 27.4 | 27.4 |

This means that the reaction is practically complete after about 3 hours.

EXAMPLE 5

3-Phenoxytoluene from K-m-cresolate and chlorobenzene

In a $N_2$ atmosphere, there were introduced: 63.75 g of 88% solid KOH=1 mol, with agitation a solution of
324.4 g of m-cresol=3 mols and
337.7 g of chlorobenzene=3 mols was added.
Subsequently, the mixture was dehydrated within about 1 hour by means of a water separator charged with 100 g of chlorobenzene. The temperature in the flask was 120°–140° C.

Subsequently, 1 g of $Cu(OAc)_2.H_2O$ (=0.005 mol) was added to the clear solution. A deeply red-brown solution was formed. After 6 hours of refluxing (140°–146° C.) the totality of the K-m-cresolate was converted to 3-phenoxytoluene.

Thereafter, 63.75 g of 88% KOH=1 mol were added to the mixture, and the batch was dehydrated in order to convert KOH to K-m-cresolate; that is, within about 1 hour 24 ml of water were separated in the water separator. After a further 6 hours of refluxing (146°–152° C.), the potassium hydroxide added further was likewise nearly quantitatively consumed for 3-phenoxytoluene synthesis, that is, the content of 3-phenoxytoluene in the reaction mixture determined by GC analysis was 360 g=1.96 mols. This corresponds to a 98% yield, relative to KOH.

EXAMPLE 6

2-Phenoxytoluene from K-phenolate and p-chlorotoluene

In the manner as described in Example 2, a solution of K-phenolate was prepared from 255 g of 88% KOH (=4 mols), 1.519 g of o-chlorotoluene (=12 mols) and 1.129 g of phenol (=12 mols). By addition of 4 g of pulverulent $CuCO_3.Cu(OH)_2.\frac{1}{2}H_2O$ (=0.017 mol), the reaction of K-phenolate and o-chlorotoluene was started at about 150° C. It was then continued under reflux at 162°–164° C. for 4 hours. By titration with acid on corresponding samples it was stated that after 2 hours 55% and after 4 hours 90% of the K-phenolate were converted. According to GC analysis, the reaction solution contained after 4 hours 650 g of 2-phenoxytoluene (=3.53 mols), which corresponds to a yield of 88.3% relative to KOH used, or a selectivity of 98% relative to reacted K-phenolate.

The solids were filtered off from the reaction mixture, and by fractional distillation via a Vigreux column having a height of 50 cm, 620 g of 2-phenoxytoluene were obtained at b.p.$_5$ 134°–135° C. with a purity of 98%, which corresponds to an isolated yield of 82.6% relative to KOH.

EXAMPLE 7

4-Chloro-4'-methyldiphenyl ether from K-p-cresolate and 1,4-dichlorobenzene

A mixture of
127.5 g of 88% KOH=2 mols
649 g of p-cresol=6 mols
1,470 g of 1,4-dichlorobenzene=10 mols, and
1,000 g of xylene (as entrainer in the dehydration) was dehydrated in the manner as described in Example 2. Subsequently, the reaction was started at about 130° C. by addition of 4 g of $CuCO_3.Cu(OH)_2.\frac{1}{2}H_2O$ and continued for about 5 hours at reflux temperature, 146°–149° C. Thereafter, 90% of the KOH were converted according to acidimetric titration, and according to GC analysis, the reaction mixture contained 355 g of 4-chloro-4'-methyldiphenyl ether, corresponding to a yield of 81.2% relative to KOH or a selectivity of 90.3% relative to reacted K-p-cresolate.

After having filtered off the solids, 320 g of 4-chloro-4'-methyldiphenyl ether were obtained at b.p.$_6$ 154° C. by fractional distillation via a Vigreux column having a height of 1.20 m, having a purity degree of 98%, which corresponds to an isolated yield of 71.8% relative to KOH:

EXAMPLE 8

4-Bromo-4'-methyldiphenyl ether and hydroquinone-di-p-tolyl ether from K-p-cresolate and 1,4-dibromobenzene A mixture of
127.5 g of 88% KOH=2 mols
432.6 g of p-cresol=4 mols
1,916 g of 1,4-dibromobenzene=8 mols and
1,050 g of xylene
was dehydrated in the manner as described in Example 2. Subsequently, 8 g of $CuCO_3.Cu(OH)_2.\frac{1}{2}H_2O$ (=0.034 mols) were added at 95° C., and the temperature of the reaction mixture was then raised again to about 140° C. With temperature rise to 160° C. by the reaction heat and heavy boiling behavior the reaction was complete after a few minutes. According to acidimetry, a KOH conversion of 98% was stated. According to GC analysis, the mixture contained 476 g of 4-bromo-4'-methyldiphenyl ether, which corresponds to a yield of 90.5% relative to KOH.

After having filtered off the solids, fractional distillation via a Vigreux column having a height of 1.20 m gave 450 g of the product of b.p.$_5$ 170° C. with a purity degree of 97%, which corresponds to an isolated yield of 83% relative to KOH.

The main by-product of the reaction is hydroquinone-di-p-tolyl ether. This by-product is formed to an increased extent when the excess of 1,4-dibromobenzene is reduced or when excess K-p-cresolate as compared to 1,4-dibromobenzene is used.

For example, when reacting in the manner of this Example a mixture of 255 g of 88% KOH=4 mols
1,298 g of p-cresol=12 mols
930 g of 1,4-dibromobenzene=3.95 mols and
1,000 g of xylene
after dehydration by addition of 4 g of CuCO$_3$.Cu(OH)$_2$.½H$_2$O (=0.017 mol), 720 g of 4-bromo-4'-methyldiphenyl ether (=2.74 mols) and 180 g of hydroquinone-di-p-tolyl ether (=0.62 mol) are formed according to GC analysis in the spontaneous reaction, that is, about 70% of the K-p-cresolate react with one bromine atom and about 30% react with both bromine atoms of the 1,4-dibromobenzene.

Hydroquinone-di-p-tolyl ether is concentrated to a large extent in the column sump on fractional distillation, and it can be obtained in pure form by recrystallization in ethanol or toluene/ethanol. M.p. 1=3° C.

EXAMPLE 9

4-Fluoro-4'-methyldiphenyl ether from p-fluorophenol and p-chlorotoluene

A mixture of
175 g of 4-fluorophenol=1.56 mols
197.6 g of 4-chlorotoluene=1.36 mols and
33.3 g of 88% KOH=0.52 mol
was dehydrated in a N$_2$ atmosphere under normal pressure, while weakly refluxing in order to prevent disturbances by foam formation. During the dehydration, the temperature in the reaction flask rose from 142° to 162° C., and the color changed from yellowish to red-brown.

After dehydration, 1 g of CuCO$_3$.Cu(OH)$_2$.½H$_2$O was added at 150° C., and the mixture was then refluxed for 1 hour (162° C.). Acidimetric supervision of the reaction proved that it was practically complete after ½ hour already:

| before catalyst addition | 0.52 mol of KOH |
|---|---|
| ½ hour later | 0.047 mol of KOH |
| 1 hour later | 0.027 mol of KOH |

The reaction mixture was cooled to room temperature, the solids were suction-filtered and washed with 3×50 ml of p-chlorotoluene. 52 g of filter cake, solvent-moist, or 44 g of dry filter cake were obtained (theory: 38.9 g=0.52 mol of KCl; Cl$^-$ 31.7%, F$^-$ 2.9%). The analysis proves that nuclear fluorine is substituted to an insignificant extent only during the reaction.

The filtrate (502 g) was fractionated via a column having a height of 30 cm and packed with 3 mm Braunschweig glass helices. At b.p.$_7$ 138° C., 60 g of 4-fluoro-4'-methyldiphenyl ether were obtained as clear liquid with a purity degree of 98%, which corresponds to an isolated yield of 57.1% relative to KOH used. Unreacted 4-fluorophenol and 4-chlorotoluene were separated in this fractionation as first runnings.

What is claimed is:

1. In a process for preparing diphenyl ethers, which includes reacting an alkali metal phenolate with a halobenzene at elevated temperature and in the presence of a copper compound as catalyst, the improvement which comprises using as the copper compound a basic copper carbonate of the formula $$xCuCO_3.Cu(OH)_2.yH_2O$$

wherein
x=1 to 2 and
y=0 to 1
and carrying out the reaction at a temperature of from about 130° to 170° C.

2. The process as claimed in claim 1, which comprises using as basic copper carbonate the compound having approximately the following composition: CuCO$_3$.Cu(OH)$_2$.½H$_2$O.

3. The process as claimed in claim 1, which comprises using the copper catalysts in an amount of from about 0.0001 to 5 mol %, relative to the alkali metal phenolate.

4. The process as claimed in claim 1, which comprises using as alkali metal phenolate an alkali metal phenolate either unsubstituted or monosubstituted by lower alkyl or fluorine.

5. The process as claimed in claim 1, which comprises using as halobenzenes mono- or dichlorobenzenes, mono- or dibromobenzenes, or monochloro- or monobromobenzene monosubstituted by lower alkyl.

6. The process as claimed in claim 1, which comprises using as halobenzenes monochloro- or monobromobenzene unsubstituted or monosubstituted by lower alkyl.

7. The process as claimed in claim 1, which comprises carrying out the reaction in the presence of an excess of the free phenol on which the alkali metal phenolate used is based.

8. The process as claimed in claim 1, which comprises using as halobenzenes mono- or dichlorobenzenes or monochlorobenzene monosubstituted by lower alkyl.

9. The process as claimed in claim 1, which comprises using as halobenzenes monochlorobenzene unsubstituted or monosubstituted by lower alkyl.

10. The process as claimed in claim 1, which comprises using the copper catalysts in an amount of from about 0.001 to 0.1 mol %, relative to the alkali metal phenolate.

* * * * *